(12) United States Patent
Gergely et al.

(10) Patent No.: US 6,432,450 B1
(45) Date of Patent: Aug. 13, 2002

US006432450B1

(54) EFFERVESCENT GRANULES WITH DELAYED EFFERVESCENT EFFECT

(75) Inventors: Gerhard Gergely, Gartengasse 8, A-1053; Irmgard Gergely; Thomas Gergely, all of Vienna (AT)

(73) Assignee: Gerhard Gergely, Vienna (AU)

( * ) Notice: Subject to any disclaimer, the term of this patent is extended or adjusted under 35 U.S.C. 154(b) by 0 days.

(21) Appl. No.: 09/656,118

(22) Filed: Sep. 6, 2000

(51) Int. Cl.[7] .................................................. A61K 9/14
(52) U.S. Cl. ..................... 424/489; 424/466; 424/490; 424/497; 514/951; 514/770; 514/784
(58) Field of Search ................................. 424/466, 465, 424/489, 490, 497

(56) References Cited

U.S. PATENT DOCUMENTS 4,093,710 A    6/1978   Sass et al. ................... 424/44
4,678,661 A    7/1987   Gergely et al. ............... 424/44

FOREIGN PATENT DOCUMENTS

| EP | 0233839 | 8/1987 |
| EP | 0642784 | 3/1995 |
| GB | 1270781 | 4/1972 |

*Primary Examiner*—James M. Spear
(74) *Attorney, Agent, or Firm*—Oliff & Berridge, PLC

(57) ABSTRACT

The effervescent granules with delayed effervescent effect consist of at least one acid component and one component evolving gas under the action of acid, as well as of active substances, fragrances, plant extracts, vitamins, minerals etc. admixed as needed, the particles of the acid component being coated with—preferably 1 to 30% by weight of—at least one carbonate compound—possibly including a partial reaction—and/or a hydrocolloid. The gas-evolving component consists of alkali hydrogen carbonate, alkali carbonate, and/or alkaline-earth carbonate particles which are coated with at least one further substance, particularly with a melt of polyethylene glycol 6000. The particles preferably have a grain size above 0.2 mm.

18 Claims, No Drawings

EFFERVESCENT GRANULES WITH DELAYED EFFERVESCENT EFFECT

The invention concerns effervescent granules with delayed effervescent effect according to the preamble of claim 1, particularly for a presentation in sachets.

Unlike known effervescent tablets, the effervescent granules packed in sachets very often are difficult to handle; when hitting the surface of the liquid, the components of the effervescent system such as citric acid and sodium hydrogen carbonate which—in order to attain rapid dissolution—most often are relatively fine-grained immediately start to react while producing effervescence. Depending on their specific weight, further components, be it adjuvants or active substances, either are retained on the surface for some time or drop to the bottom, and poorly dissolve there. This effect is further amplified when the granules are poured from a commercial type of sachet, which in most cases is close to square-shaped and for this reason has a relatively wide tear opening (occasionally in the size range of the liquid surface). The components of the effervescent mix then hit a correspondingly large part of the liquid surface as a relatively thin layer.

It has been the aim of the invention, therefore, to develop effervescent granules with delayed effervescent effect that are readily and freely flowing. Due to their specific packaging, these granules offer consumer-friendly handling and may contain vitamins, minerals, trace elements or pharmaceutically active substances as well as sweeteners and flavors. The aim was a simple preparation which would allow the product to be manufactured at a favorable price, and granules to be obtained which drop to the bottom without reacting when introduced into (water, and produce their effervescent effect, only after several seconds at the bottom, thus producing turbulence in the liquid which achieves dissolution of active substances or vitamins, minerals and other ingredients with very small quantities of these delayed-action effervescent mixes.

From EP-A1-642,784 a coating of the carbonate particles is known which serves for a better fixation of the pharmaceutically active substance, exactly on these carbonate particles. This effervescent mix would yield an insufficient delay relative to the aim of the present invention.

In EP-A1-233,839, an effervescent mix is described in which both components imperatively are coated with xanthan, which is not readily soluble and hence leads to dissolution times of up to 35 min, a time entirely useless for the present aims.

In GB-A1-1,270,781, it is described in a few examples that for the purposes of improved stability, not only the acid component but also the carbonate component of the effervescent mix be coated with very slight amounts of polyethylene glycol and HPMC (hydroxypropylmethylcellulose). This again would lead to a delay that is highly insufficient for the purposes of the present invention.

The object of the present invention is surprisingly well achieved according to the invention by the actions listed in claim 1. Advantageous further embodiments of the invention are described in the characteristics of the dependent claims.

It was seen that the passivation and the coarse-grained structure of the organic acids such as citric and tartaric acid yield some effect, but this is far from adequate for the purposes of attaining a sufficient delay in the effervescent effect.

It is necessary, therefore, to delay or process the gas-evolving components of the carbonate phase in the effervescent system, that is, the alkali and/or alkaline-earth carbonates and/or alkali hydrogen carbonates, in such a way that one can achieve the desired effect, viz., a distinctly delayed effervescent action upon introduction into the water and an effervescent effect evolving from the bottom.

In general, the retarding substances can be sugars, sugar alcohols or colloids which are applied to the particles of the alkaline, gas-evolving: mixture of carbonates and bicarbonates and yield a delay effect after drying.

An effect particularly suitable for this system is achieved by polyethylene glycols, which produce satisfactory delay effects in effervescence because of the time during which they themselves take up water, and also because of their interference with the reaction. In preference, polyethylene glycol 6000 is employed; mixtures of polyethylene glycol 4000 with polyethylene glycol 10,000 can also be employed. A satisfactory quantity to be employed in order to achieve the desired effect proved to be 5 to 15 percent by weight referred to the gas-evolving components. To the fused polyethylene glycol one can add further substances such as colloids, for instance very fine gum guar powder or xanthan, as well as a micronized acid component. A micronized, poorly soluble acid component such as fumaric or adipic acid that has been introduced into the melt leads to the advantage that overly agglomerated granules of the alkali hydrogen carbonates and alkali carbonates or alkaline-earth carbonates can readily dissolve. Here a charge of 1 to 3 percent by weight relative to the gas-evolving components or 10 to 30 percent relative to the polyethylene glycol charge will suffice.

The gas-evolving substances can now be granulated with alcoholic solutions of polyethylene glycols, and then dried. This approach produces an appropriate delay of the effervescent effect, already in a mixture with a citric acid treated with alkaline-earth carbonate.

It is a particularly preferred preparative approach for the purposes of attaining a delay to mix and homogenize these gas-evolving carbonates and/or bicarbonates and then slowly add fused polyethylene glycols to the mixture at a high temperature, preferably drop by drop. At high temperatures of about 120 to 160 ° C., polyethylene glycols need more time to solidify, hence sufficient time is available during the mixing for coating of the individual particles with a film of polyethylene glycol. It is advisable then, of course, to select coarse-grained alkaline components and for instance use a coarse-crystalline form of the granular sodium carbonate or sodium hydrogen carbonate, since such particles sink more rapidly, which produces a delayed effervescent effect from the bottom. Sodium hydrogen carbonate, potassium hydrogen carbonate, sodium carbonate, potassium carbonate as well as magnesium carbonate are suitable here.

It has been found to be advantageous in the case of sodium hydrogen carbonate to select a grain size distribution where the major sieve fraction is in the range between 0.1 and 0.4 mm, preferably to the extent of 50 to 85% and particularly preferably to the extent of 70 to 85%. For potassium hydrogen carbonate, a grain size of <0.5 mm is recommended, although the main portion of the particles should be above 0.1 mm. In view of the poorer solubility of sodium carbonate, this can be employed in a finer quality, for instance with the main portion of the grains between 0.07 and 0.2 mm. Calcium carbonate is preferably used in an amount of up to 30% by weight of the gas-evolving components.

A further improvement of the system can be achieved, as indicated earlier, by the appropriate superficial passivation of the acids, preferably with calcium or magnesium salts, which leads to an additional delay of the reaction start.

For active substances such as paracetamol, lactulose, N-Acetylcysteine, ranitidine, plant extracts, multivitamins and/or trace elements, for instance, an organic acid treated with 1 to 10% by weight of calcium carbonate can serve as the acid component to which the alkali hydrogen carbonates, alkali carbonates, and/or alkaline-earth carbonates that have been delayed in their effervescent effect are then added as described above. This yields, on one hand the desired, delayed effervescent effect and on the other hand the intended stability.

For products intended to contain trace elements, the same basic approach can be conceived, since the composition according to the invention does not need any additional action to incorporate the trace elements.

In the case of calcium and/or magnesium products, the corresponding alkaline-earth carbonate or oxide can be used to treat the organic acid. The amount of calcium and/or magnesium that must additionally be introduced, largely depends on the desired doses of calcium and magnesium ions; in the instance of calcium, for instance, granulated or precipitated calcium carbonates having corresponding flow properties can be incorporated in addition into the alkaline carbonate phase. In the case of magnesium products, one can either apply up to 30% by weight of magnesium carbonate to the organic acid particles or add trimagnesium dicitrate to the final mix, in order to reach the desired amount of magnesium ions.

The preferred acid component is citric acid having a main sieve fraction of 50 to 95% by weight within grain sizes of 0.3 to 0.7 mm. It is particularly preferred to use citric acid grit with a relatively coarse grain, the grain sizes of the main sieve fraction (about 80%) being between 0.3 and 0.6 mm. Coarser grain sizes may retard the reaction too much. With an appropriate passivation of the grains, one can also use a somewhat finer citric acid, for instance one having the main sieve fraction of 50 to 95% by weight within grain sizes of 0.2 to 0.4 mm, in order to obtain the desired product. The preferred grain size will lastly depend, not only on the rate of dissolution of the acid and gas-evolving components selected, but also on the final formulation and on other active substances incorporated into the granules. For instance, the citric acid can be mixed with 1 to 10% by weight of calcium carbonate and then brought in contact with a solution producing superficial passivation and thus, on one hand the delayed effervescent effect and on the other hand an enhanced stability of the granules is attained. The solution used to treat the mixture of citric acid and calcium carbonate (which has for instance a particle size of <5 $\mu$m, the preferred size being 0.1 to 0.2 $\mu$m) can be an aqueous or alcoholic or aqueous-alcoholic solution of citric acid containing between 40 and 80% by weight of citric acid in. the solution.

It is possible, too, to employ an aqueous buffer-granulating solution according to European Patent No. 0,272,312. For an even stronger delay of the effervescent effect, hydrocolloids can be employed. These can either be applied after moistening of the mixture of organic acid with carbonate, where an amount of 1 to 5% by weight is preferable. Or one can introduce the hydrocolloids into the granulating solution, in which case smaller amounts of 0.1 to 1% by weight are required. Maltodextrins, polyvinylpyrrolidone, gum guar, gum arabic and all hydrocolloids soluble in water, ethanol or their mixtures can be employed as hydrocolloids.

Treatment of the organic acids can be performed with all current, technically known methods such as fluidized-bed driers, vacuum granulators as well as continuous reaction systems. If necessary, the organic acid after the treatment can be dried to secure optimum stability.

After the treatment the dried organic acid is screened to a grain size of 1 to 2 mm. Acid thus treated is mixed in a final mixing step with the carbonate phase and with the active substances, vitamins and/or minerals and/or trace elements. With an additional amount of alkali carbonates or alkali hydrogen carbonates one can also set a desired pH value.

This basic mixture can be provided with all current, permitted sweeteners such as aspartame, sodium cyclamate, saccharin sodium salt, acesulfame as well as the corresponding fragrances and flavors. When needed, fillers which in their grain size distribution match the basic granules can be introduced, for instance sugars or sugar alcohols such as mannitol, sorbitol, xylitol etc.; granulated maltodextrins can also be used as fillers.

In this system, relatively large amounts of soluble active substances can be dissolved on account of the vortex action initiated at the bottom. It is for instance possible to dissolve 10 g of lactulose with about 3 to 4 g of the granulated mixture of citric acid coated with calcium carbonate in combination with the carbonate phase.

This system also yields satisfactory dissolution behavior for granulated plant extracts usually having a very strong lump and slime-forming tendency. Depending on their properties, the plant extracts may merely be admixed to the system, for instance Echinacea, Agnus castus, ivy and Cimicifuga. It is recommendable, however, to perform an additional step by treating the extract with an antifoaming or wetting agent, which improves the vortex formation and the effect of the granules dissolving with a delay from the bottom.

The active substances can be integrated into the system in the most diverse manners. In the case of water-soluble active substances, admixing to the effervescent mix components usually will suffice. Depending on their sensitivity to acids or alkaline components, small amounts of the active substances can bei introduced, either into the citric acid component or into the carbonate phase, in order to be uniformly distributed in the granules.

Through its special effervescent effect, the system reveals an extremely good dispersing action even for insoluble active substances such as paracetamol. In the case of an active substance that is very poorly wettable or present in large amounts, it may become necessary to apply a special treatment to it and then introduce it as an individual phase.

For vitamin products such as vitamin C or multivitamin products, a dry mix of the treated citric acid with the carbonate phase and the vitamin C or, for the multivitamin products, with the multivitamins can be prepared which is then packed, preferably into special elongated sachets.

A further advantage of the effervescent system according to the invention is brought out by a special packaging in tubular long sachets. The sachets are preferably made in a width of 10 to 30 mm and a length of 7 to 20 cm. The amount of effervescent granules that is required depends on the active substances that should be incorporated. The weight of a sachet may for instance be 1 g if only small amounts of active substances are to be dissolved. In the case of effervescent mineral mix sachets which should contain a given amount, for instance, of calcium or magnesium, it will be necessary to use the appropriate amount of citric acid in order to set the desired pH value, so that the effervescent mineral mix sachets may weigh as much as 4–5 g. These elongated sachets have the advantages of a more consumer-friendly handling and more rapid penetration of the granules into the water, juice or mixed drinks, since the granules hit the liquid surface as a thin, concentrated jet which, because of the delayed effervescent effect, does not react at once producing effervescence but swiftly passes through the surface, drops to the bottom of the cup and only there starts to effervesce. This is an additional device for preventing effervescence of the effervescent granules upon first contact with the water surface and floating of the granules on the surface prior to their sinking and generating the effervescent effect.

It was found as a surprise that with a citric acid thus treated, and with the carbonate phase, one can achieve, both the desired retardation of the effervescent effect and a stability meeting the requirements of the ICH guidelines. On the other hand, the elongated sachet contributes substantially to the applications of the pharmaceutical form, since the granules are not spread flat on the water surface but fall to the bottom of the cup as if through a pipe, and develop their effervescent action only from there.

Exemplified embodiments of the invention are cited in the following examples.

EXAMPLE 1

Preparation of Passivated Citric Acid

The preparation can occur in a fluidized-bed drier or in a vacuum granulator.

A mixer is filled with 1940 parts by weight of citric acid grit and 60 parts by weight of calcium carbonate, which are homogeneously mixed. To this mixture are added 20 parts by weight of a pre-reaction solution consisting of 13 parts by weight of citric acid, 3 parts by weight of calcium carbonate and 15 parts by weight of water, and distributed homogeneously for about 3 min. Then another 11 parts by weight of the pre-reaction solution are added and distributed homogeneously for 5 min, leading to partial reaction on the citric acid grit surface. This moistened mixture is introduced into a fluidized-bed drier and dried to a residual moisture content of 0.1% at 70° C. Then the granules are screened to a grain size of 1.0 to 2.0 mm.

When using a vacuum granulator for the preparation one proceeds in the same manner, but it is recommended to heat the citric acid and calcium carbonate to 60° C. before introducing the solution. The drying occurs at 60° C. in a vacuum of 15 mbar.

EXAMPLE 2

Preparation of a Carbonate Phase With Delayed Reaction

A mixer is filled with 1000 parts by weight of coarsely crystalline sodium hydrogen carbonate and 200 parts by weight of calcium carbonate. The two starting materials are homogeneously mixed, then 120 parts by weight of a polyethylene glycol melt heated to 130° C. are added while stirring, and distributed homogeneously. After cooling, the carbonate granules are screened to a grain size of 1.6 mm.

An optimum formulation for achieving, both a delay and a turbulent effervescent effect, was found when further adding to the melt of 120 parts by weight of polyethylene glycol, 20 parts by weight of micronized fumaric acid as well as 36 parts by weight of xanthan gum and 2.4 parts by weight of Aerosil, and if needed 10 parts by weight of Miglyol 812® (a neutral vegetable oil). After cooling, the carbonate granules are screened to a grain size of 1.6 mm.

From the basic granulated products of Examples 1 and 2, the most diverse formulations can be prepared, for instance:

EXAMPLE 3

Vitamin C Effervescent Granules With Delayed Effervescent Effect consist of 1400 parts by weight of passivated acid component, 980 parts by weight of the carbonate phase, and 180 parts by weight of ascorbic acid, 934 parts by weight of sorbitol as well as sweeteners and fragrances as needed. A dose of 3.6 g, which may be packed in long sachets, contains 180 mg of ascorbic acid and drops to the bottom when introduced into water. It is only 2 to 5 s later that the granules start to effervesce, and finally dissolve completely.

EXAMPLE 4

Multivitamin Effervescent Granules

Multivitamin effervescent granules can be prepared in the same way, and if required packed in long sachets, while adding vitamins according to the daily recommendations, as well as sweeteners, and if required colorants and fragrances.

EXAMPLE 5

Calcium Effervescent Granules With 250 mg Calcium Exhibiting Retarded Reaction

In this case, too, a citric acid phase passivated with calcium carbonate can be used, as described in Example 1, the amount of calcium additionally required being contained in the carbonate phase. Here either calcium carbonate granules or precipitated calcium carbonate with a coarser grain structure can be utilized.

The carbonate granules are prepared as in the analogous Example 2. In a mixer, 904 parts by weight of coarsely crystalline sodium hydrogen. carbonate are mixed and homogenized with 628 parts by weight of a 36%, granulated calcium carbonate, then the polyethylene glycol 6000 melt is introduced at a temperature of 130° C. while stirring, and distributed homogeneously. The melt consists of 108.5 parts by weight of polyethylene glycol 6000, 2 parts by weight of Aerosil 200, 32 parts by weight of Keltrol F, 9 parts by weight of Miglyol 812® and 18 parts by weight of fumaric acid. After cooling the granules are screened to a grain size of 1.6 mm.

From the components of the passivated citric acid and the carbonate phase, a final product can be prepared that consists of 2000 parts by weight of passivated citric acid, 1702 parts by weight of the carbonate phase, 689 parts by weight of sorbitol, 6 parts by weight of saccharin sodium salt, 50 parts by weight of orange fragrance and 2 parts by weight of No. 6 Yellow for coloration.

A dose of 4.5 g contains 250 mg of calcium; it is packed in a long sachet and shows an appropriately delayed dissolution when introduced into water.

EXAMPLE 6

Magnesium effervescent granules

The citric acid grit is treated with about 30% (by weight, referred to the citric acid grit) of magnesium carbonate. The citric acid passivation can again be performed, either in a granulator, in a fluidized-bed drier or in a vacuum granulator.

In a mixer or granulator, 560 parts by weight of citric acid grit are mixed and homogenized with 178 parts by weight of magnesium carbonate, and heated to 60 ° C. This mixture is then wetted with 120 parts by weight of a 50% aqueous citric acid solution, and homogenized for 10 min, during which time a partial reaction and passivation takes place. The product is then dried, either in the fluidized-bed drier or in vacuum, and after drying screened through a 1.25-mm sieve.

For the final product, the carbonate phase cited in Example 2 can be utilized.

For a dose of 5 g containing 7.5 mmole of magnesium, 2960 parts by weight of the citric acid that was passivated with magnesium carbonate are mixed with 1388 parts by weight of the carbonate phase as well as 560 parts by weight of sorbitol. Sweeteners and fragrance are added to this mixture as needed. This final mixture is packed in long sachets and reveals excellent properties with reference to the delayed effervescent effect and good dissolution.

Using the system of delayed effervescent effect one can dissolve large amounts of soluble active substances with a small amount of effervescent granules, since the granulated mix, containing the active substance sinks to the bottom and the active substance is dissolved by vortex action due to the relatively vigorous reaction starting at that point.

EXAMPLE 7

Lactulose Effervescent Granules

For a dose containing 10 parts by weight of lactulose, 1.76 parts by weight of the citric acid that was passivated with calcium carbonate as described in Example 1 are utilized and homogeneously mixed with 1.23 parts by weight of the carbonate phase as well as 10 parts by weight of lactulose, and provided with sweeteners and fragrance.

A dose of 13 g contains 10 g lactulose; the product when introduced into water first sinks to the bottom and there starts to effervesce vigorously after 3 s, whereupon all of the lactulose is dissolved. It is also possible to use 4 g of the two components, which leads to an even better effervescent effect.

EXAMPLE 8

Lactulose With Electrolyte Ions

Amongst other consequences, a diuretic leads to a loss of ions such as calcium, sodium, potassium, and magnesium, hence it is possible to incorporate these ions into the carbonate granules and readminister them with the product.

About 90 to 100 mg calcium ions, 100 mg potassium ions, and 90 mg magnesium ions can be incorporated with 270 mg sodium ions into a dose of 14 to 15 g containing 10 parts by weight of lactulose. To this end, 2124 parts by weight of coarsely crystalline citric acid are mixed in a mixer or granulator with 356 parts by weight of magnesium carbonate, and heated to 60° C. This mixture is wetted with 250 parts by weight of an aqueous 50% citric acid solution, which is then homogeneously distributed during 10 min while a partial reaction and passivation takes place. The product is then dried and after drying screened to 1.5 mm.

In parallel, the following approach is taken to prepare a delayed carbonate phase: 237 parts by weight of calcium carbonate, 830 parts by weight of sodium hydrogen carbonate, 100 parts by weight of sodium carbonate and 267 parts by weight of potassium hydrogen carbonate are homogeneously mixed. Into this mixture a melt consisting of 142 parts by weight of polyethylene glycol, 42 parts by weight of Keltrol, 2.8 parts by weight of Aerosil, 12 parts by weight of Miglyol 812 and 24 parts by weight of micronized fumaric acid and heated to 130° C. is introduced while stirring, and homogenized. After cooling, the granules are screened to a grain size of 1.6 mm.

For the finished product, 2480 g of the treated citric acid, 1647 g of the treated carbonate granules, and 10 kg lactulose as well as sweeteners and fragrance are added and mixed homogeneously. The granules are packed in sachets containing 14.2 g each. When introduced into water they first sink to the bottom and there start to effervesce after 3 s, whereupon all of the lactulose is dissolved within about 40 s and yields a solution of pleasant taste.

EXAMPLE 9

Acetylcysteine 600 mg Effervescent Granules

Following the approach of Example 2, 700 parts by weight of the passivated citric acid of Example 1 are mixed with 600 parts by weight of acetylcysteine and 700 parts by weight of a "delayed" carbonate phase containing in addition to the calcium carbonate and sodium hydrogen carbonate another 10% (by weight referred to the sodium hydrogen carbonate) of sodium carbonate. To this mixture one can also add the corresponding sweeteners and fragrances.

Two to 2.1 g of this mixture sink to the bottom when introduced into water, start to effervesce after about 2 to 3 s, and the active substance dissolves completely within 30 s during the effervescence.

EXAMPLE 10

Paracetamol 1000 mg Effervescent Granules

It is recommended to prepare a proper phase of the active substance in addition to the two phases as cited in Examples 1 and 2 when larger amounts of a poorly wettable active substance are to be incorporated into the formulation.

For a dose of 5 g containing 1 g paracetamol, the following phase of active substance is prepared: 1500 parts by weight of mannitol and 100 parts by weight of sodium hydrogen carbonate are mixed homogeneously, and heated to 50° C. Then a solution consisting of 40 parts by weight of polyvinylpyrrolidone K30 and 0.2 parts by weight of docusate sodium in 250 parts by weight of ethanol is introduced into the mixer and distributed homogeneously for wetting. Finally 1000 parts by weight of paracetamol are added, whereupon the entire mixture is once more wetted with a solution consisting of 100 parts by weight of polyethylene glycol 6000 in 250 parts by weight of ethanol. The product is vacuum-dried and then screened to a grain size of 0.3 mm.

Then the final granulated mix is prepared from 2740 parts by weight of the paracetamol phase, 740 parts by weight of the passivated citric acid, and 1060 parts by weight of the carbonate phase which are mixed homogeneously with 216 parts by weight of sorbitol; further are added 60 parts by weight of aspartame as well as 83 parts by weight of fragrance and 100 parts by weight of a mannitol/simethicone phase. Five gram of this product, packed in sachets, sink to the bottom when introduced into water, then effervesce and disperse the paracetamol homogeneously in the solution.

This system can also be used to prepare plant extract effervescent granules, while certain extracts may necessitate preparation of a proper phase for the plant extract. However, a number of plant extracts exist which can be mixed directly with the basic granulated mixes described in Examples 1 and 2 to produce an appropriate dissolution pattern:

EXAMPLE 11

Plant extract effervescent granules 350 parts by weight of dry Echinacea extract are mixed with 1400 parts by weight of passivated citric acid as well as 980 parts of "delayed" carbonate phase and 934 parts by weight of sorbitol. The appropriate sweeteners and the fragrance are added. A dose of 3.5 to 3.6 g shows the desired effect of dropping and effervescing with vortex action from below, through which the Echinacea extract is dissolved.

EXAMPLE 12

Effervescent Granules With Amino Acid, Vitamins, Calcium and Magnesium

For preparation of the acid phase, 2400 parts by weight of crystalline citric acid as well as 50 parts by weight of crystalline ascorbic acid are mixed with 240 parts by weight of calcium carbonate. This mixture is wetted with 160 parts by weight of a monosodium citrate solution (pre-reaction solution) and partly reacted. An additional 174 parts by weight of magnesium oxide can be introduced and wetted with another 120 parts by weight of the same solution, so that the magnesium oxide partly reacts. Then an alkaline sodium hydrogen carbonate/sodium carbonate phase is prepared by first mixing 300 parts by weight of coarsely crystalline sodium hydrogen carbonate with 100 parts by weight of sodium carbonate. Onto this mixture, 60 parts by weight of a melt of polyethylene glycol 6000 heated to 130° C. are spread.

Additional calcium carbonate can be added to this phase in order to obtain a higher calcium dose.

For the finished product, 2856 parts by weight of the acid phase as well as 460 parts by weight of the alkaline phase are mixed with 500 parts by weight of arginine aspartate as well as vitamins, sweeteners, colorants and fragrances. A dose of 4.3 g then contains 500 mg arginine aspartate, desired doses of the B vitamins, vitamin C, and vitamin E, as well as calcium and magnesium. The granules drop to the bottom when introduced into water, and there start to effervesce, whereupon the soluble active substances are dissolved within 40 s through the effervescent effect.

What is claimed is:

1. Effervescent granules with delayed effervescent effect, consisting of at least one acid component and one gas-evolving component of alkali hydrogen carbonate, alkali carbonate, and/or alkaline-earth carbonate particles evolving gas under the action of acid, as well as of active substances, fragrances, plant extracts, vitamins, minerals admixed as needed, the at least one acid component comprising particles coated with at least one of the following compounds: alkali carbonate, alkali hydrogen carbonate, alkaline-earth carbonate, alkaline-earth oxide, hydrocolloid, wherein the particles of the gas-evolving component are coated with a melt of polyethylene glycol or mixtures of polyethylene glycols.

2. Effervescent granules according to claim 1, wherein the melt contains at least one colloid and/or at least one micronized acid.

3. Effervescent granules according to claim 1, wherein at least 50% by weight of the particles of the acid component have a grain size above 0.2 mm.

4. Effervescent granules according to claim 1, wherein the gas-evolving components contain up to 30% by weight of alkaline-earth carbonate, the remainder being sodium hydrogen carbonate which is present to the extent of 50 to 85% by weight in a grain size between 0.1 and 0.4 mm and/or sodium carbonate in a grain size of 0.7 to 0.2 mm.

5. Effervescent granules according to claim 1, containing a magnesium salt as the active substance in an amount of up to 30% of the acid component.

6. Effervescent granules according to claim 1, containing electrolytes in order to balance ion losses.

7. Effervescent granules according to claim 1, containing an active substance that is insoluble in water.

8. Effervescent granules according to claim 1, containing dry plant extracts.

9. Effervescent granules according to claim 1, containing at least one water-soluble active substance and/or a vitamin and/or trace elements.

10. Effervescent granules according to claim 1, wherein the effervescent granules are present in a sachet having a length between 5 and 20 cm and a width between 6 and 30 mm.

11. Effervescent granules according to claim 1, wherein the gas-evolving component coating allows the effervescent granules to arise from 2 to 10 s after the introduction into water.

12. Process for the preparation of a gas-evolving component of effervescent granules with delayed effervescent effect, wherein particles of the gas-evolving component are coated with a polyethylene glycol film by adding a melt of polyethylene glycol at a temperature of 120–160° C. to a homogenous mixture of alkali and/or alkaline-earth carbonates or hydrogen carbonates, and this melt is mixed with the alkali and/or alkaline-earth carbonates.

13. Effervescent granules according to claim 1, wherein the polyethylene glycol is polyethylene glycol 6000.

14. Effervescent granules according to claim 1, wherein the melt of polyethylene glycol or mixture of polyethylene glycol is in an amount of 5 to 15% by weight of the gas-evolving component.

15. Effervescent granules according to claim 2, wherein the micronized acid is present in an amount of 10 to 30% by weight of the polyethylene glycol.

16. Effervescent granules according to claim 2, wherein the micronized acid is fumaric acid or adipic acid.

17. Effervescent granules according to claim 5, wherein the magnesium salt is selected from the group consisting of magnesium oxide, magnesium carbonate and magnesium dicitrate.

18. Effervescent granules according to claim 11, wherein the effervescent effect arises 4 to 6 s after introduction into water.

* * * * *

UNITED STATES PATENT AND TRADEMARK OFFICE
CERTIFICATE OF CORRECTION

PATENT NO.    : 6,432,450 B1                                              Page 1 of 1
DATED         : August 13, 2002
INVENTOR(S)   : Gerhard Gergely et al.

It is certified that error appears in the above-identified patent and that said Letters Patent is
hereby corrected as shown below:

<u>Title page,</u>
Item [73], Assignee: "Gerhard Gergely, Vienna (AU)" should read
-- Vienna (AT) --.

The following should be inserted:

-- [30] Foreign Application Priority Data
September 9, 1999     (EP)     99117762.7 --

Signed and Sealed this

Seventh Day of January, 2003

JAMES E. ROGAN
*Director of the United States Patent and Trademark Office*